United States Patent
Itani

[19]

[11] Patent Number: 5,837,198
[45] Date of Patent: Nov. 17, 1998

[54] PHYSIOLOGICAL TISSUE TREATMENT APPARATUS

[75] Inventor: Kazunori Itani, Mitaka, Japan

[73] Assignee: Aloka Co., Ltd., Tokyo, Japan

[21] Appl. No.: 771,799

[22] Filed: Dec. 20, 1996

[30] Foreign Application Priority Data

Dec. 28, 1995 [JP] Japan .................................. 7-343944
Nov. 29, 1996 [JP] Japan .................................. 8-319566

[51] Int. Cl.⁶ ................................................. G01N 35/10
[52] U.S. Cl. .......................... 422/63; 422/65; 422/101; 422/104; 436/47; 436/48; 436/49; 436/177
[58] Field of Search .............................. 422/63, 99, 100, 422/65, 101, 102, 104; 436/43, 49, 174, 177, 180, 183

[56] References Cited

U.S. PATENT DOCUMENTS

| | | | |
|---|---|---|---|
| 4,120,547 | 10/1978 | Price et al. ............................... | 312/209 |
| 4,557,903 | 12/1985 | McCormick ............................ | 422/101 |
| 4,738,824 | 4/1988 | Takeuchi .................................. | 422/63 |
| 4,885,253 | 12/1989 | Kralovic .................................. | 435/296 |
| 5,108,707 | 4/1992 | Glenney .................................. | 422/99 |
| 5,273,905 | 12/1993 | Mullet et al. ........................... | 435/301 |
| 5,310,674 | 5/1994 | Weinreb et al. ........................ | 435/293 |
| 5,427,742 | 6/1995 | Holland .................................. | 422/102 |
| 5,462,874 | 10/1995 | Wolf et al. .............................. | 435/297 |
| 5,468,638 | 11/1995 | Barker et al. .......................... | 435/304.1 |
| 5,532,168 | 7/1996 | Marantz .................................. | 436/176 |
| 5,543,114 | 8/1996 | Dudek .................................... | 422/102 |
| 5,573,727 | 11/1996 | Keefe ...................................... | 422/63 |
| 5,650,323 | 7/1997 | Root ...................................... | 435/284.1 |

*Primary Examiner*—Long V. Le
*Attorney, Agent, or Firm*—Fishman, Dionne, Cantor & Colburn

[57] ABSTRACT

When reagent was discharged in a physiological tissue reagent treatment apparatus, it was troublesome to retain the sample so that it was not discharged together with the reagent. This apparatus offers an improvement on this point, saves work involved in reagent treatment and enables lower costs to be attained. Samples 70 are held in separate sample containers 8. The base of this sample container 8 comprises a mesh 64. Consequently, when the sample container 8 is inserted in a reagent bath 6 in which reagent has collected, reagent flows from this mesh 64 into the container 8. Reagent may flow also from a flow hole 66. The reagent which has flowed into the container 8 acts on the sample 70, and reagent treatment takes place. The reagent in a plurality of the sample containers 8 set in a container holder 10, is then aspirated by a pump 30, or by a nozzle inserted together with the container 8 in the reagent bath, via the mesh 64 of the container. The adjacent reagent baths 6 are mutually independent, and reagent is injected only into the reagent bath 6 to be used for the reaction. Only contaminated sample containers 8 are discarded as necessary.

13 Claims, 9 Drawing Sheets

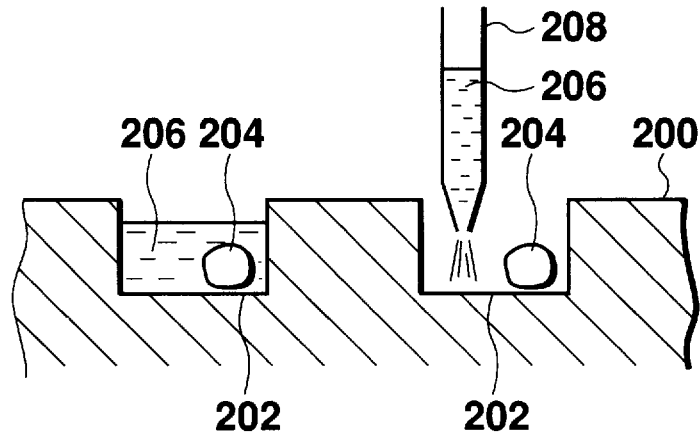
Fig. 12 (a) PRIOR ART
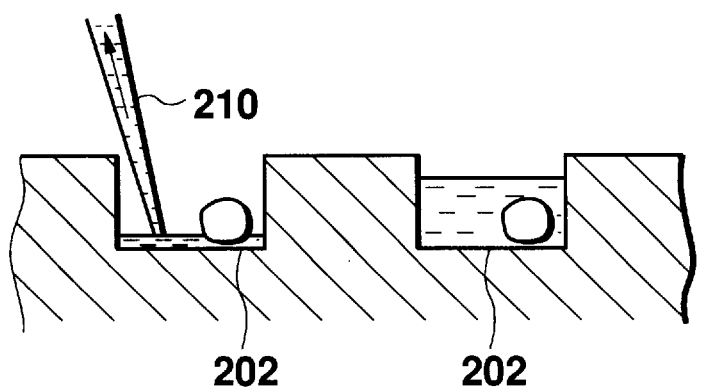
Fig. 12 (b) PRIOR ART

PHYSIOLOGICAL TISSUE TREATMENT APPARATUS

BACKGROUND OF THE INVENTION

1. Field of the Invention

This invention relates to an apparatus for treating physiological tissue samples with a reagent, and in particular to an apparatus which saves labor in the treatment of minute tissue samples with a reagent.

2. Description of the Prior Art

Conventionally, immunological staining procedures or ISH (in situ hybridization) of physiological tissue samples were conducted by mounting a section of the sample on a slide and reacting it with a reagent, or by hole mounting of mainly small specimens such as chicken embryos.

FIGS. 12(a) and 12(b) are illustrations of a conventional hole mount procedure. In conventional hole mounting, a micro-plate 200 comprising 24 holes or 96 holes was used.

A specimen 204 is set in a recess referred to as a hole 202, and a reagent 206 is injected by a pipette 208 into the hole 202 (FIG. 12(a)). To promote reaction between the reagent 206 and specimen 204, the micro-plate 200 is mounted on an agitating device to agitate the reagent 206 or the whole micro-plate 200 is placed in an incubator to keep it at a suitable temperature. When the reagent procedure is finished, the reagent is removed from the aforementioned hole 202 by aspiration using a very thin glass tube 210 connected to a pump. In the above immunological staining and ISH procedures, injection of reagent, reaction and aspiration is repeated several times.

In the aforesaid method, when the reagent 206 is aspirated from the hole 202 of the micro-plate 200, it is necessary to restrain the specimen, e.g. by forceps, so that the specimen is not aspirated. This operation was not suitable for automation and so was performed by hand, which was very inefficient. The problem is moreover aggravated the smaller the specimen. The amount of work caused by this problem is in direct proportion to the number of samples and kinds of reagents used for treatment. In particular, in genetic screening research and testing, large numbers of samples have to be prepared, and a labor-saving device for preparing samples was therefore desired.

Further, when a sample group subjected to reagent treatment on one microplate was divided into a plurality of sub-groups, and it was then desired to subject these sub-groups to different procedures, e.g. procedures performed at different temperatures, the operator had to transfer the sub-groups to different microplates using forceps or the like which involved a great deal of work. To minimize the need to wash apparatus, there is also a preference to use disposable containers. In this case, however, microplates have to be discarded even when only one hole has been used due to the risk of reagent splashes, and this resulted in high cost.

SUMMARY OF THE INVENTION

It is therefore an object of this invention to reduce the human effort involved in reagent treatment of physiological tissue samples, make the operations and apparatus used more flexible, reduce contamination in reagent procedures, reduce cost and provide an apparatus suitable for mass preparation of samples.

The apparatus for treatment of physiological samples according to this invention comprises a reagent bath for collecting reagent and a container for holding samples which is inserted in and withdrawn from this reagent bath. The apparatus comprises at least one sample container part or all of which is formed from a mesh material finer than the size of the samples.

When a sample container is inserted in the reagent bath according to this invention, a reagent in the reagent bath is supplied to the sample container through the aforesaid mesh, and reacts with the sample. When the sample container is lifted out of the reagent bath, the reagent in the sample container drains off through the mesh. In a preferred form of this invention, it is the base of the sample container which comprises the aforesaid mesh material. In another preferred form of the invention, the sample container has a flow hole formed at a predetermined height which connects the interior with the exterior of the container.

A preferred form of this invention comprises a reagent rack provided with a plurality of reagent baths, different sample containers being inserted in different reagent baths.

In the apparatus for treatment physiological tissue according to this invention, the reagent bath comprises a container insertion part which receives the sample container, and a nozzle insertion part connected with the container insertion part which receives a nozzle to drain reagent off.

According to this invention, a nozzle can be inserted in the reagent bath at the same time as the sample container is inserted in the reagent bath. Therefore when for example a plurality of reagent-sample reactions are performed, the nozzle may be used to inject, drain and change reagents while the container is in the reagent bath.

In a preferred form of this invention, the sample container comprises a mesh in its base, and the reagent bath comprises a reagent flow passage extending from the lower part of the mesh to the base of the inserted part of the nozzle.

In another preferred form of this invention, the reagent bath also comprises a reagent drain port which drains off reagent.

According to the physiological tissue treatment apparatus of this invention, therefore, treatment reagent can be drained off without any need for concern that the sample will be aspirated, hence treatment operations are rendered more efficient. Moreover, as there is no need to restrain the sample with forceps or the like, the sequence of steps from injection of reagent into the reagent bath to reaction and drainage can be automated, hence the apparatus reduces the work involved in treating large numbers of samples.

Even when only some of the treatment performed on a plurality of samples is the same, the samples may be treated in their own sample containers so there is more flexibility of operation.

Only sample containers which have become contaminated need be discarded, so the cost of reagent treatment is lowered.

The physiological tissue treatment apparatus according to this invention is therefore suitable for reagent treatment of large numbers of samples.

BRIEF DESCRIPTION OF THE DRAWINGS

FIGS. 12(a)–12(b) are descriptive drawings of a conventional hole mount.

DESCRIPTION OF THE PREFERRED EMBODIMENTS

Embodiment 1

A preferred form of this invention will now be described with reference to the drawings.

Figure 1:
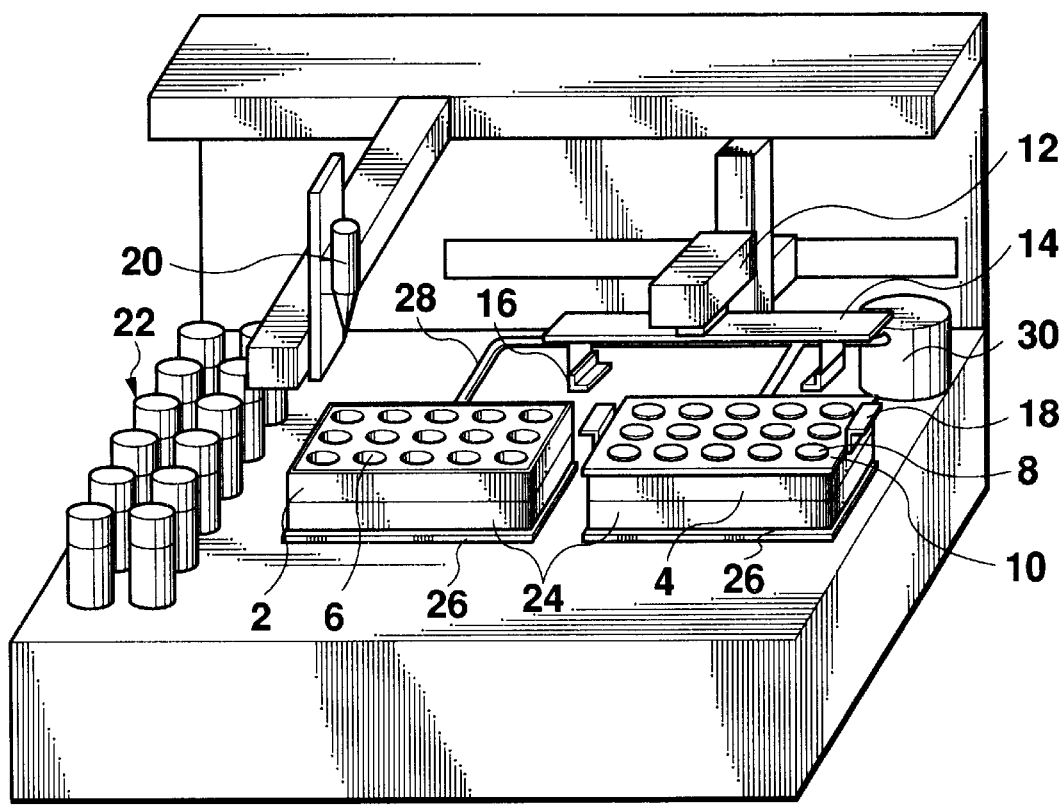
FIG. 1 is a perspective view showing an outline of a physiological tissue sample treatment apparatus according to a first embodiment of this invention.

FIG. 1 is a perspective view showing, in outline, a physiological tissue treatment apparatus according to this invention. An apparatus which can simultaneously process a plurality of samples is shown here. Two reagent racks 2 and 4 are provided so that a plurality of sample types can be treated efficiently. Each reagent rack has 15 holes, and each of these holes forms a reagent bath 6 which is described hereafter. A container holder 10 comprising a plurality of sample containers 8 is inserted in the reagent rack 4.

A container displacing mechanism (holder displacing mechanism) 12 comprises a hanger 14 free to move in three directions, i.e. up/down, forward/back and left/right. A claw 16 of the hanger slides underneath a hook 18 of the container holder 10 so as to lift it up and support the holder 10. The sample containers 8 can thereby be moved integrally with the container holder 10. A pipette head 20, which is also formed such that it can be displaced in three directions, aspirates a suitable amount of a required reagent from a reagent table 22, and injects it into the reagent bath 6. A temperature controller 24 such as a heater is provided underneath the reagent racks 2, 4, and an agitator 26 is provided under this temperature controller 24.

A description of a reagent treatment using this apparatus will now be given. After a reagent is introduced into the reagent baths 6 in one of the reagent racks by the pipette head 20, the container holder 10 is moved by the displacing mechanism 12 so as to insert the sample containers 8 into the reagent baths 6 filled with reagent. Reagent then flows into the sample containers 8, and a reaction takes place between the samples in the containers 8 and the reagent in the baths 6. The temperature controller 24 adjusts the reagent temperature in the baths 6 and the agitator 26 vibrates the reagent racks 2, 4 so as to promote or control the reagent reactions.

The apparatus comprises the two racks 2, 4 so that treatment by different reagents may be carried out continuously. Specifically, while a reaction is taking place between a sample and a reagent in one of the racks, e.g. the reagent rack 2, another reagent may be introduced into the baths 6 in the other rack 4 using the pipette head 20 to prepare for the next reagent reaction. Reagent treatment and injection may thus be carried out in parallel so that operating time is shortened. Also, even when a reagent is used at a predetermined temperature to promote a reaction, the temperature adjustment process may be performed in parallel so that the time is again shortened.

The sample reaction begins when all the samples are introduced together by the container holder 10 into the reagent baths 6 which already contain reagent. Hence even when there are a plurality of samples, correct conditions such as reaction times can be established for all samples. By contrast, according to the conventional technique, the reagent was successively injected into holes containing samples in a microplate. The reaction start times were therefore different for each hole, and samples awaiting reagent injection tended to become dry or hard so that it was more difficult to make them react with the reagent. This easily led to scatter of reaction conditions within one microplate. However by providing two reagent racks, reagent treatment by a plurality of reagents can be performed effectively in a short time, and the reaction conditions for a plurality of samples can be made uniform. As described hereafter, a reagent drain port is provided in the bath 6. After reaction, the reagent is drained from the bath 6 by an aspirating means comprising a tube 28 and pump 30 connected to this drain port.

Figure 2:
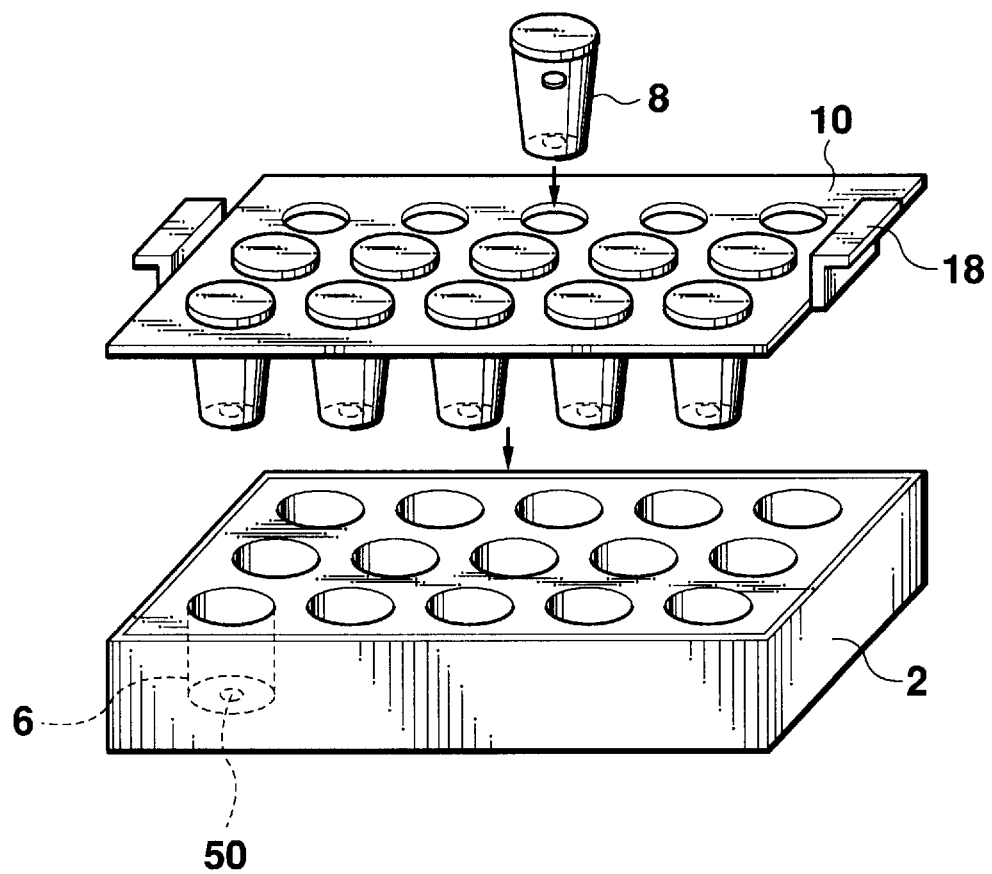
FIG. 2 is a perspective view showing the essential construction of a reagent rack, container holder and sample containers.

FIG. 2 is a perspective view showing the essential construction of the reagent racks 2, 4, the container holder 10 and the sample containers 8. The reagent bath 6 provided in the reagent racks 2, 4 has a cylindrical recess of, for example, diameter 15 mm and depth 15 mm. Adjacent baths 6 are isolated from each other so that reagent can be introduced into them separately. A reagent drain port 50 is provided in the base of the reagent bath 6. The container holder 10 is formed of a metal such as aluminum or stainless steel, or a resin such as Teflon or Acryl, and it comprises rows of circular openings of diameter 14 mm into which the sample containers 8 are inserted.

Figure 3:
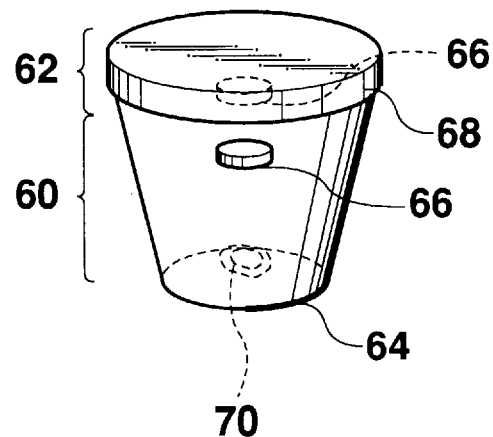
FIG. 3 is a perspective view showing the essential construction of a sample container.

FIG. 3 is a perspective view showing the schematic construction of one of the sample containers 8. The sample container 8 comprises a conical cup 60 and a lid (cap) 62, these members being formed of resin. The cup dimensions are correlated with the dimensions of the container holder 10, e.g. the diameter of the upper aperture is 14 mm, the diameter of the base is 10 mm and the depth of the cup is 12 mm. According to this embodiment, the base of the cup 60 is formed of a nylon mesh 64 having openings of 0.4 mm. These openings must be smaller than the size of the sample to be treated, it being expedient to use cups having different mesh sizes according to the size of samples. Flow holes 66 having a diameter of 1–3 mm are provided at two positions in the upper part of the lateral wall of the cup 60. This flow hole 66 is intended to assist flow of reagent into the container 8 even when reagent cannot easily permeate the sample container 8 from the mesh due to the fineness of the mesh, etc. In other words, if reagent does not permeate the container 8 when the container 8 is inserted in the bath 6, the liquid level outside the container 8 will rise, and reagent may then be supplied to the container 8 from the flow hole 66. It is desirable that this flow hole 66 is at such a height that it is above the liquid level even when the amount of reagent required for treatment has flowed into the container. This is because if the hole 66 were lower than the liquid level in the container 8, any sample floating inside the container 8 could flow out of the container 8 from the hole 66. The number of these flow holes 66 is arbitrary. The upper part of the cup 60 comprises a circumferential projection 68 extending towards the side. When the container 8 is inserted in an opening in the container holder 10, it engages with the holder 10 due to this projection 68. A sample 70 larger than the size of the mesh 64 is placed by forceps on the mesh 64 of the cup 60, and the lid 62 is then fitted to the cup 60. The lid 62 and cup 60 may also be joined together, e.g. the lid 62 may be made to engage with or screw into the projection 68. As the diameter of the cup 60 is made smaller towards its base, it is easy to place the sample in the cup 60 and remove it from the cup 60 after treatment using forceps as described above. Further, by making the diameter of the base of the cup 60 smaller than the opening of the bath 6, the container 8 may easily be inserted in the bath 6 even when the displacement precision of the mechanism 12 is poor.

The container 8 shown here comprises the flow hole 66, and this hole 66 adjusts the pressure inside the container 8. There is consequently little risk that reagent flow into the container 8 will be stopped due to the accompanying rise of pressure in the container. In some cases, however, the size of the mesh may be sufficiently large so that it is unnecessary to provide the flow hole 66. In such cases, it may be arranged that the lid 62 does not completely cover the upper part of the container 8, and the pressure in the container may be adjusted by using a lid with air holes.

Figure 4:
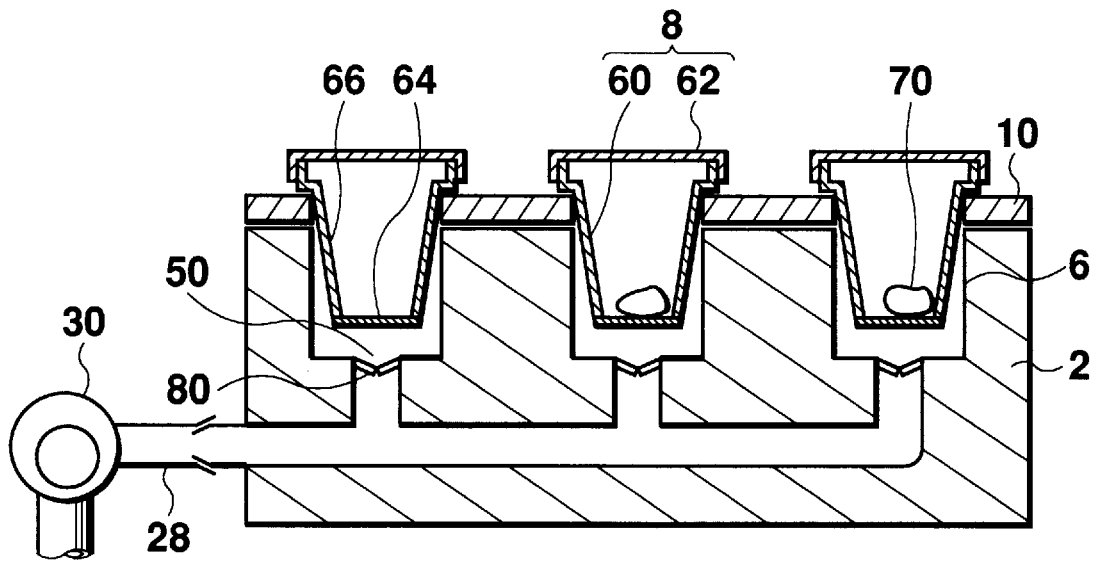
FIG. 4 is a schematic view in section of a reagent rack in which a plurality of sample containers are inserted using said container holder.
Figure 5:
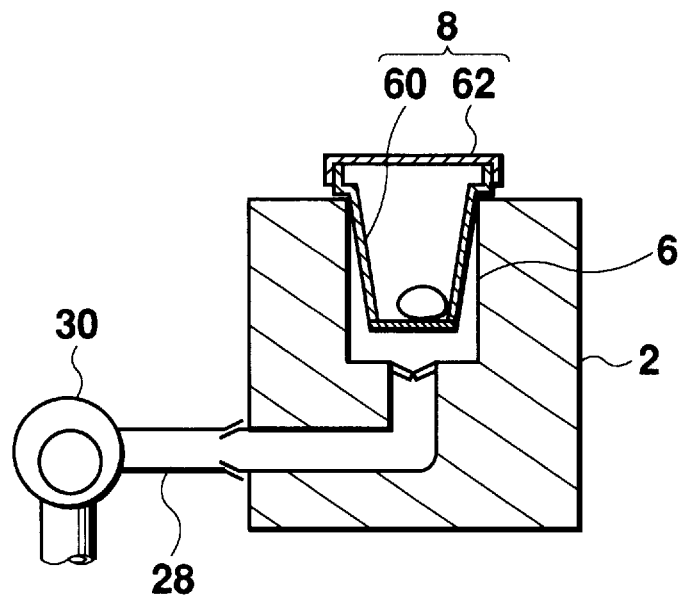
FIG. 5 is a schematic view in section of a reagent bath in which a sample container is inserted.

FIG. 4 and FIG. 5 are schematic views in section of baths 6 into which sample containers 8 are inserted. FIG. 4 shows the case where the inserted containers 8 are resting on the container holder 10. A reagent drain port 50 is connected to the pump 30 via the tube 28. A drain port valve 80 provided in the drain port 50 controls accumulation and drainage of reagent, prevents excessive discharge of reagent from the port 50 and thereby economizes the amount of reagent used. The valve 80 may for example be an electromagnetic valve. It will be understood that when the number of samples is small, the apparatus may be designed such that the containers 8 are inserted separately in the baths 6 without using the container holder 10, as shown in FIG. 5.

Figure 6:
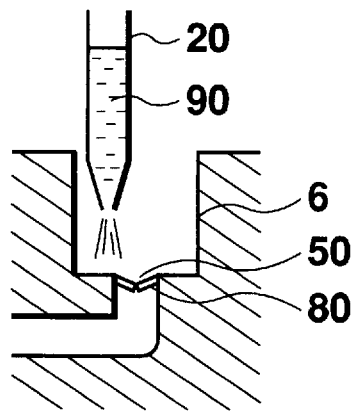
FIGS. 6(a)–6(g) are schematic views in section describing reagent treatment in a reagent bath.
Figure 6:
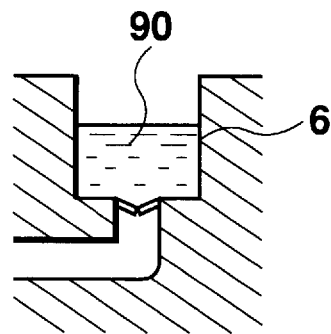
Figure 6:
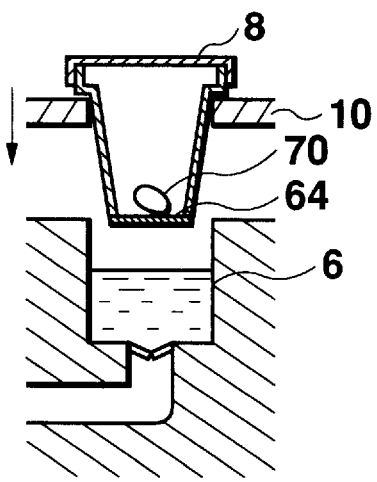
Figure 6:
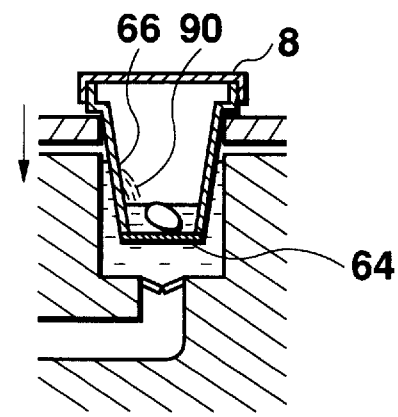
Figure 6:
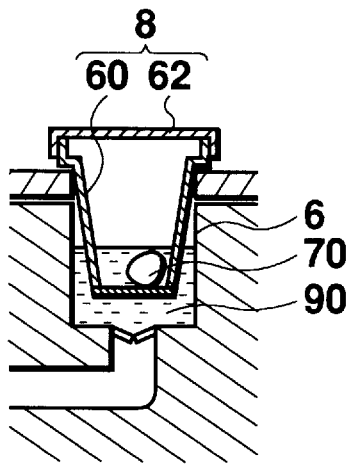
Figure 6:
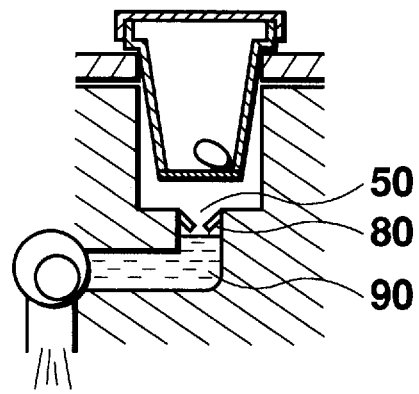
Figure 6:
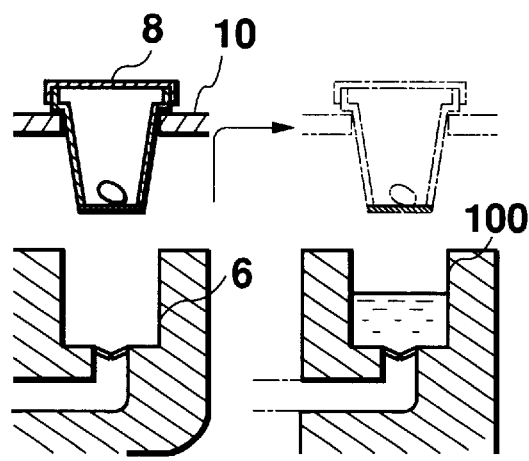

FIGS. 6(*a*)–6(*g*) are schematic views in section describing the treatment which takes place in the reagent bath 6 of this apparatus. The treatment steps will be described in the order of FIG. 6(*a*)–6(*g*). The pipette head 20 moves into the opening of the bath 6, and injects a reagent 90 into the bath 6 (FIG. 6(*a*)). The drain port valve 80 opens when the pump 30 aspirates, and shuts when the pump 30 stops.

In the above reagent injection step, the pump 30 stops and closes the valve 80, so the injected reagent 90 accumulates in the bath 6 (FIG. 6(*b*)). The mechanism 12 displaces the container holder 10 so that the container 8 resting on the holder 10 is positioned exactly above the bath 6, and then lowers it into the bath 6 (FIG. 6(*c*)). When the container 8 is introduced into the reagent 90, reagent flows into the container through the mesh 64. It may be difficult for the reagent to permeate the container due to the fineness of the mesh 64, however in this case the reagent 90 is blocked by the container 8, its level rises to the flow hole 66, and it then flows into the container 8 through the hole 66 (FIG. 6(*d*)). The sample 70 is allowed to react with the reagent 90 for a predetermined time, the reaction being promoted by using the temperature controller 24 and agitator 26. When the reaction proceeds for a long time, and especially when heat is applied by the temperature controller 24, evaporation of the reagent cannot be ignored, but as the lid 62 of the container 8 closes the openings of the cup 60 and bath 6, decrease of reagent due to evaporation is suppressed (FIG. 6(*e*)). When the reaction is complete, the pump 30 begins aspiration. The valve 80 then opens, and the reagent 90 is aspirated from the drain port 50 (FIG. 6(*f*)). While the sample is reacting with the reagent in the bath 6 of one of the reagent racks in the step shown in FIG. 6(*e*), the steps shown in FIG. 6(*a*), (*b*) are performed in a reagent bath 100 in the other reagent rack, and a reagent to be used next collects in the bath 100. The container 8 is then moved from the bath 6 to the bath 100 by the container displacing mechanism 12 (FIG. 6(*g*)), and the same processing is performed as that of the steps shown in the diagrams FIG. 6(*c*)–6(*f*). In this manner, treatment with required reagents is performed by moving the container 8 to and from the two reagent racks 2, 4. When all reagent treatment is complete, the sample 70 is withdrawn from the container 8.

As the container can be separated from the holder 10, the whole container is moved even when a sample group that has been subjected to a given reagent treatment is divided and different reagent treatments are subsequently performed. It is therefore unnecessary to grasp the sample 70 with forceps and move it to another container, so operations are made very simple. Although it is possible to wash the container 8 in order that it can be re-used, there is a preference to use disposable equipment to avoid this procedure and prevent contamination due to imperfect washing. However, in the case of conventional equipment, it was exceedingly uneconomical to throw away a 96 hole microplate in order for example to treat only one sample, and it was also troublesome to have to treat samples individually with other equipment. According to this apparatus, however, only the number of samples actually treated by reagent is consumed even when the number to be treated on one occasion is small. The operation is therefore rendered less costly, and the aforesaid preference to avoid washing is also satisfied.

Further, as the baths 6 in the reagent racks are separated from each other, reagent need be injected into the baths 6 only as much as necessary depending on the number of samples. Less reagent is therefore required, again lowering the cost. Treatment with different reagents may also be performed on each bath in the same reagent rack.

Figure 7:
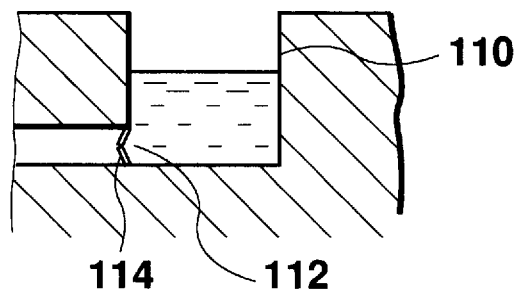
FIG. 7 is a schematic view in section showing a reagent bath comprising a reagent drain port fitted with a drain port valve in the lower part of a lateral surface of the bath.
Figure 8:
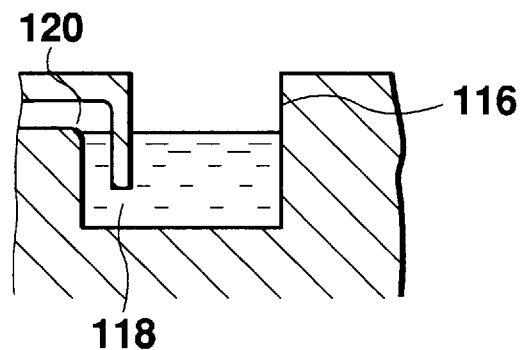
FIG. 8 is a schematic view in section showing a reagent bath comprising a reagent drain port without a drain port valve in the lower part of a lateral surface of the bath.

FIG. 7 and FIG. 8 are schematic diagrams in section of other forms of reagent bath. A reagent bath 110 shown in FIG. 7 comprises a reagent drain port 112 in a lateral surface of the base, a drain port valve 114 being provided in this port 112. A reagent bath 116 shown in FIG. 8 comprises a reagent drain port 118 in a lateral surface of the base. A pipe 120 which is connected to this port 118 and has an upper bend, is situated at a higher position than the port 118. In this case, although no drain port valve is provided in the drain port 118, collection of reagent in the bath 116 and its discharge from the bath 116 is controlled solely by the operation of the pump 30. Regarding the methods used to collect reagent, one method is to temporarily position the pipe 120 higher than the liquid surface of the reagent to be collected. Another method is to temporarily open the pipe on the side of the pump 30 to restore the pipe 120 to atmospheric pressure, and then to close the pipe on the pump side.

The functions of the aforesaid reagent drain port and aspirating means are firstly to promote drainage of reagent from the sample container, and secondly to drain reagent from the reagent bath. When the first function is not required as when for example the mesh size of the sample container is large, a drain port need not be provided in the reagent bath and the second function may be implemented by another method. For example, when reagent treatment has been completed in one of the two reagent racks, the sample container may be moved to the other reagent rack, and spent reagent aspirated by a capillary tube from an opening in the upper part of the reagent bath. In this case, as there is no sample in the bath when the reagent is aspirated, it is unnecessary to restrain the sample with forceps to prevent it being aspirated as was done in the prior art, and the operation may therefore easily be automated. In this case, the baths and the reagent rack have extremely simple constructions as there are no drain ports. For example, microplates may be provided having deep holes into which the sample containers are inserted, and if these are made disposable together with disposable containers, a still higher degree of protection from contamination is offered.

Figure 9:
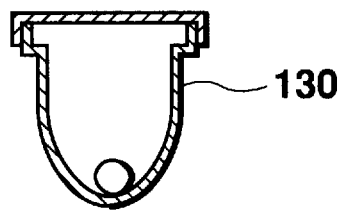
FIG. 9 is a schematic view in section showing another example of a sample container having a taper shape.

FIG. 9 is a schematic view of another embodiment of this invention. A sample container 130 has the shape of a cup with an axial plane of symmetry and tapering towards the base which is inserted into a reagent bath. The shape of the container is however not limited to the aforesaid conical or tapering axially symmetrical shape, a variety of shapes being possible such as for example a shape having a rectangular horizontal cross-section.

Embodiment 2

Another preferred embodiment of the invention will now be described with reference to the appended drawings. In the following description, component elements having the same function as those of the preceding first embodiment are given the same symbols and their detailed description is omitted.

Figure 10:
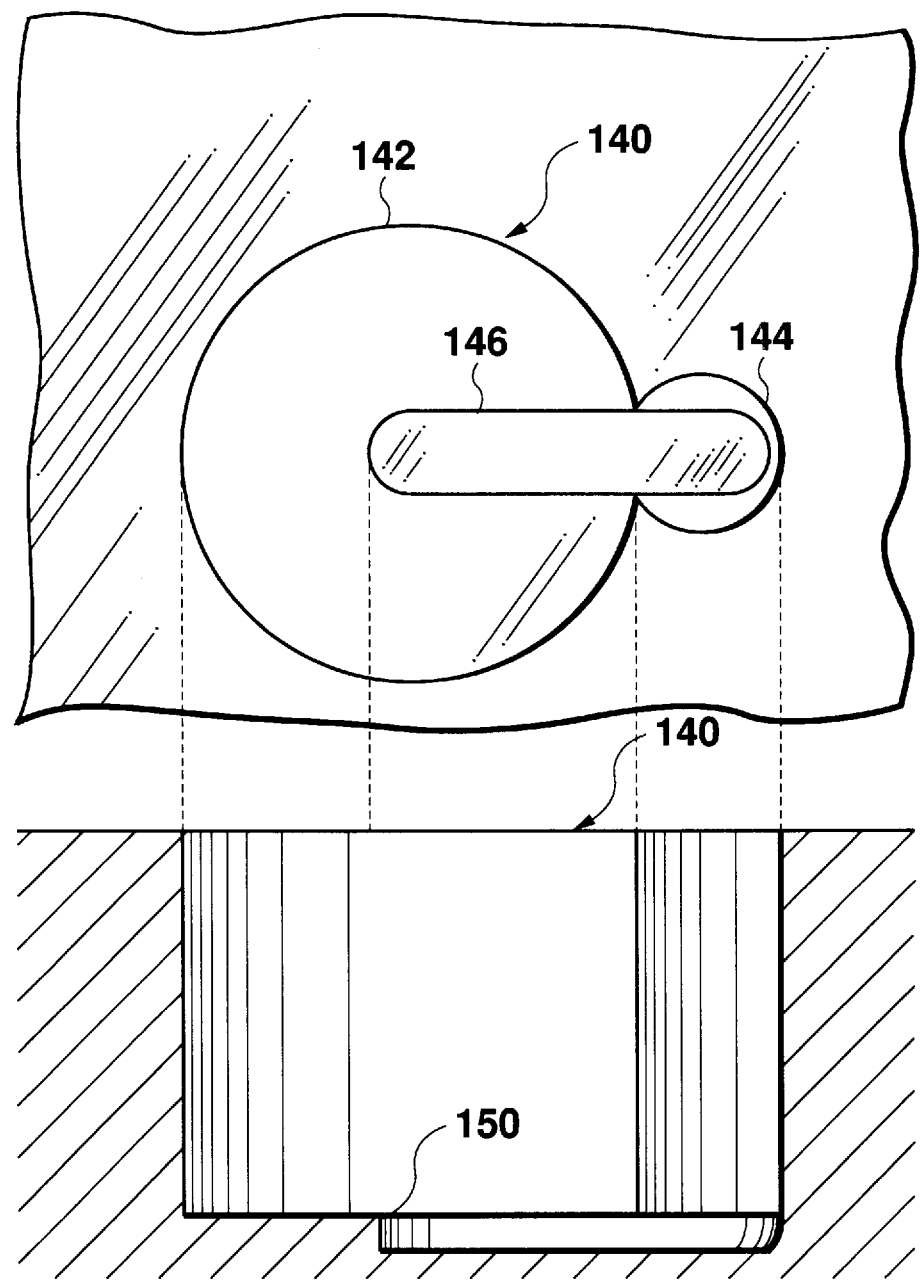
FIG. 10 is a descriptive drawing of the structure of a reagent bath according to a second embodiment of this invention.

The main feature of this embodiment is the way in which reagent is drained from the reagent bath. FIG. 10 describes the structure of a bath 140 according to this embodiment, the upper part of the drawing being a plan view and the lower part being a view in section. The bath 140 broadly comprises two parts, i.e. a container insertion part 142 in which the container 8 is inserted and a nozzle insertion part 144. These two parts are joined together forming a one-piece construction. Part of the base of the container insertion part 142 is cut away to form a groove 146. This groove 146 extends to the base of the nozzle insertion part 144.

Figure 11:
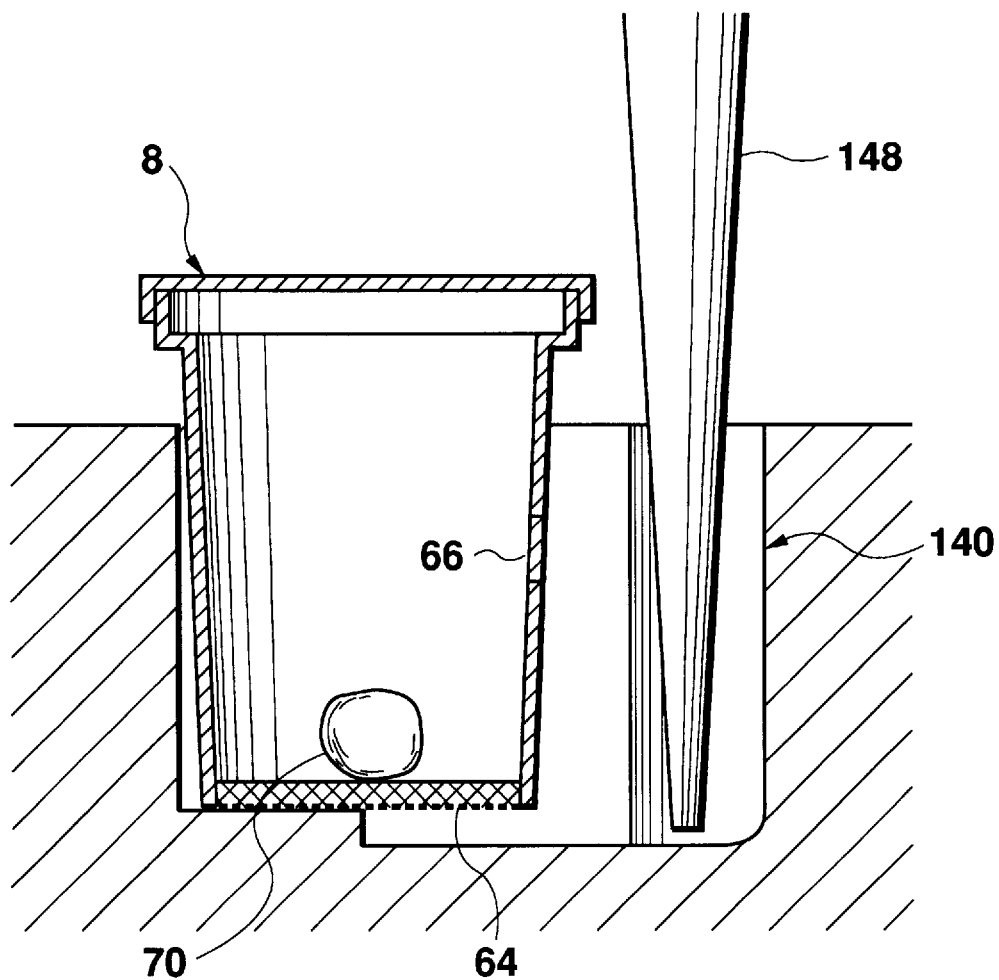
FIG. 11 is a schematic view in section of a state when a sample container and a nozzle are inserted in a reagent bath.

FIG. 11 is a section of a state wherein the container 8 and a nozzle 148 are inserted in the bath 140. A distinctive feature of this embodiment is that the container and nozzle may be simultaneously inserted into the reagent bath.

The nozzle 148 is fitted to, for example, the tip of a pipette head 20. The nozzle 148 is inserted in the bath 140, and reagent is injected into the bath 140 or withdrawn from the bath 140 by the aspiration/discharge force of the pipette head 20.

In a container 8 wherein the height of the cup 60 is less than the depth of the bath 140, a projection 68 of the container 8 comes in contact with the upper opening of the bath 140 before the base of the container 8 comes in contact with a ridge 150 so that further insertion of the container 8 is prevented. Alternatively, in the case of a container 8 wherein the height of the cup 60 is greater than the depth of the bath 140 or a container without the projection 68, the base of the container comes in contact with the ridge so that further insertion of the container is prevented. Therefore, in the case of the bath 140, there is always a minimum clearance due to the groove 146 at the base whichever container is used. The inside and outside of the container 8 are connected through the mesh 64 of the container base which is situated above this groove 146. The depth of the groove 146 is of the order of, for example, 1 mm.

The groove 146 extends to the nozzle insertion part 144, so reagent injected from the nozzle 148 flows through this groove 146 to reach the mesh 64 in the base of the container 8, and permeates the interior of the container 8 from there. On the other hand, when the nozzle 148 aspirates, reagent flows from the container 8 through the groove 146 so as to reach the nozzle 148, and is then discharged. Hence due to the groove 146, the base of the container 8 does not entirely come in close contact with the base of the bath 140, and reagent can therefore flow smoothly between the interior and exterior of the container 8.

In discharging reagent from the bath 140, from the viewpoint of completely discharging the reagent, it is desirable that the tip of the nozzle 148 is inserted as far as possible, i.e. inserted to the base of the nozzle insertion part 144.

In the figure, the case has been shown where the flat plane contour of the groove 146 is thin and long, however provided the ridge 150 is present so that the base of the container 8 comes into contact with the ridge to prevent further insertion as described above, the groove may have any plane contour. In order to avoid stagnation of reagent during discharge, it is preferred that the base of the groove 146 is smooth and flat. For the same reason, the groove 146 may be shaped so that it gradually deepens towards the nozzle insertion part 144.

In FIG. 10, the case was shown where the nozzle insertion part 144 has a flat plane contour depending on the horizontal section of the nozzle, and the container insertion part 142 is clearly distinct from the nozzle insertion part 144. Basically however, provided that the container 8 and nozzle 148 can be simultaneously inserted, the bath 140 may have any flat plane contour. It may also assume a shape wherein the distinction between the container insertion part 142 and nozzle insertion part 144 is not clear from the external appearance, such as a simple circle or rectangle. It will be noted that when the bath 140 has a large planar contour, it will be able to accommodate various sample containers and nozzles, but it should also be remembered that the amount of reagent required will also be greater.

In the physiological tissue treatment apparatus using the reagent bath 140 and sample container 8 according to this embodiment, it is unnecessary to restrain the sample by forceps so that it is not aspirated by the nozzle especially when reagent is discharged. Therefore when the construction of this embodiment is applied to a treatment apparatus wherein an operator inserts a sample container into a reagent bath, and withdraws or inserts a nozzle, reagent treatment efficiency is greatly improved. This embodiment may also be applied to an automated treatment apparatus. A schematic outline of such an automated apparatus may be of the type shown in for example FIG. 1, comprising the container displacing mechanism 12 for inserting the container 8 into the reagent bath 140 and the pipette head 20 free to move in three directions. In this case, the tip of the pipette head 20 corresponds to the nozzle 148. In such an automated apparatus, separate pipette heads may be provided for injecting reagent into the bath 140 and discharging reagent from the bath 140. Further, in this automated apparatus, a movable pipette head 20 may be provided alone without the container displacing mechanism 12.

What is claimed is:

1. A physiological tissue treatment apparatus for treating physiological tissue samples with a reagent, comprising:

a reagent bath for collecting said reagent, a least one sample container inserted in and withdrawn from said reagent bath, said sample being held in the interior of said sample container, and at least part of said sample container being formed of a material of finer mesh than the size of said sample, wherein said reagent bath comprises a sample container insertion part for accommodating said sample containers, and a nozzle insertion part communicating with said sample container insertion part for accommodating a nozzle for discharging said reagent.

2. A physiological tissue treatment apparatus as defined in claim 1, wherein the base of said sample container is formed of said mesh material.

3. A physiological tissue treatment apparatus as defined in claim 1, wherein said sample container comprises on its side an auxiliary flow hole connecting the interior with the exterior of said sample container at a predetermined height, said sample container being immersed in said reagent collected in said reagent bath.

4. A physiological tissue treatment apparatus as defined in claim 1, wherein a part of said sample container inserted in said reagent bath has a shape which tapers towards its base.

5. A physiological tissue treatment apparatus as defined in claim 1, wherein said sample container comprises a lid which closes its upper opening.

6. A physiological tissue treatment apparatus as defined in claim 1, wherein a reagent rack comprising a plurality of said reagent baths is provided and said sample containers are each inserted in different reagent baths.

7. A physiological tissue treatment apparatus as defined in claim 1, wherein the upper opening of said reagent bath and the outer wall surface of said sample container come in close contact when said sample container is inserted in said reagent bath.

8. A physiological tissue treatment apparatus as defined in claim 1, wherein said sample container comprises said mesh in its base, and said reagent bath comprises a reagent flow passage extending from the lower part of said mesh to the base of said nozzle insertion part with said sample container inserted in said reagent bath.

9. A physiological tissue treatment apparatus as defined in claim 1, wherein a container displacing mechanism is provided for inserting said sample container in, and withdrawing it from, said reagent bath.

10. A physiological tissue treatment apparatus as defined in claim 9, wherein two reagent baths are provided for each sample container, said container displacing mechanism moves said sample container between said two reagent baths, and when said sample container is inside one of said reagent baths, reagent discharge and injection are performed in the other of said reagent baths.

11. A method of using a physiological tissue treatment apparatus according to claim 1, comprising:
pouring said reagent into said reagent bath;
inserting said sample container in said reagent bath, so as to immerse said sample held in said sample container in said reagent; and
discharging said reagent retained in said reagent bath through said nozzle by inserting said nozzle in said nozzle insertion part, while said sample container is inserted in said reagent bath.

12. A physiological tissue treatment apparatus as defined in claim 1, further comprising a container holder having an aperture into which said sample container may be inserted from above, wherein a projection is formed in the upper part of said sample container so that it rests in said aperture.

13. A physiological issue treatment apparatus as defined in claim 12, further comprising a holder displacing mechanism which displaces said container holder, wherein all of said sample containers held in said container holder are inserted in and withdrawn from said reagent bath together.

* * * * *